United States Patent [19]

Wang et al.

[11] Patent Number: 4,559,400

[45] Date of Patent: Dec. 17, 1985

[54] POLYMER FROM AROMATIC DIAMINE AND N,N,N',N'-TETRAGLYCIDYL-1,3-PROPYLENE BIS(P-AMINOBENZOATE)

[75] Inventors: David W. Wang, Vestel, N.Y.; Daniel R. Draney, Norwalk, Conn.

[73] Assignee: American Cyanamid Company, Stamford, Conn.

[21] Appl. No.: 677,135

[22] Filed: Feb. 6, 1985

Related U.S. Application Data

[62] Division of Ser. No. 518,856, Aug. 1, 1983, Pat. No. 4,518,786.

[51] Int. Cl.[4] ............................................. C08G 69/08
[52] U.S. Cl. ................................... 528/327; 528/321; 528/331; 528/407
[58] Field of Search ..................... 528/327, 321, 331

[56] References Cited

U.S. PATENT DOCUMENTS

| | | | |
|---|---|---|---|
| 2,629,733 | 2/1953 | Weisblat et al. | 549/552 |
| 3,932,360 | 1/1976 | Cerankowski et al. | 260/77.5 AM |
| 4,269,759 | 5/1981 | Edelman | 260/42.17 |
| 4,451,645 | 5/1984 | Johncock | 549/552 |
| 4,518,786 | 5/1985 | Wang et al. | 549/552 |

*Primary Examiner*—Harold D. Anderson
*Attorney, Agent, or Firm*—William H. Calnan; Steven Hultquist

[57] ABSTRACT

Polymers of a polyfunctional epoxy compound, N,N,N',N'-tetraglycidyl-1,3-propylene bis(p-aminobenzoate), formed by reaction of such epoxy compound with aromatic polyamines. The disclosed polymers are useful as structural resins, e.g., as advanced composite matrix resins.

2 Claims, No Drawings

POLYMER FROM AROMATIC DIAMINE AND N,N,N',N'-TETRAGLYCIDYL-1,3-PROPYLENE BIS(P-AMINOBENZOATE)

This is a division of application Ser. No. 518,856 filed Aug. 1, 1983, now U.S. Pat. No. 4,518,786.

FIELD OF THE INVENTION

This invention relates to a new and useful compound. More particularly, it provides N,N,N',N'-tetraglycidyl-1,3-propylene bis(p-aminobenzoate) which is useful as an epoxide resin.

BACKGROUND OF THE INVENTION

CROSS REFERENCE TO RELATED APPLICATIONS

This application is related to the following concurrently filed applications:

| Attorneys Docket | Serial No. | Applicant(s) |
|---|---|---|
| 110–031 (28,954) | 518,872 | D. W. Wang, J. L. Courter, D. K. Kohli. |
| 110–033 (29,457) | 518,873 | K. Hirschbuehler. |
| 110–034 (29,054) | 518,874 | K. Hirschbuehler, D. K. Kohli. |
| 110–035 (29,458) | 518,879 | D. R. Draney, D. K. Kohli. |

DESCRIPTION OF THE PRIOR ART

Polyfunctional epoxy resins derived from aromatic polyamines are known, e.g., from U.K. Pat. No. 907,844, and they can be cured with aromatic polyamines to form structural resins.

SUMMARY OF THE INVENTION

It has now been found that a tetraglycidyl derivative of 1,3-propanediol bis-(p-aminobenzoate), and its homopolymers, can be prepared, that it has utility, for example, as an epoxy resin prepolymer, and that the polyaddition products thereof with aromatic polyamines have advantageous properties.

DESCRIPTION OF THE INVENTION

According to the present invention, there are provided N,N,N',N'-tetraglycidyl-1,3-propylene-bis(p-aminobenzoate), and homopolymers thereof.

DESCRIPTION OF THE PREFERRED EMBODIMENT

The following example illustrates the preparation and demonstrates use of the compound of this invention, and its homopolymers.

EXAMPLE 1,3-propylene bis-(p-aminobenzoate), 314.34 g. (U.S. Pat. No. 3,932,360) is dissolved in a mixture comprising 1560 g. of epichlorohydrin, 500 ml. of ethanol, and 50 ml. of water at about 23° C., then the mixture is heated to 80° C. with stirring for 40 hours. Sodium hydroxide solution, 400 g. of 50% by weight in water, is added dropwise over 45 min. during which the temperature reaches 65° C. The temperature is subsequently maintained at 60°–65° C. for 4 hours. The liquid is decanted and the solid is washed with methylene chloride. The combined filtrate and washings are vacuum stripped at 65° C. to leave a viscous residue. This is dissolved in 500 ml. of $CH_2Cl_2$, 250 ml. of $H_2O$ and 250 ml. of methyl isobutyl ketone. The organic layer is separated and washed with water (3×500 ml.). The solution is dried with anhydrous magnesium sulfate, filtered, and the solvent is vacuum stripped to a final temperature of 130° C. The product, a viscous oil, weighs 497 g., 92% of theoretical. Epoxy equivalent weight is 152–153 g./epoxide group. The compound has the formula:

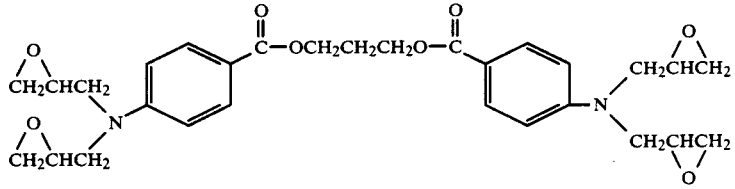

Mixing the compound at a ratio of 1.0 epoxide equivalents with 0.75 NH-amine equivalents of, respectively, diaminodiphenyl sulfone (Composition A) and 1,3-propanediol bis-(p-aminobenzoate) (Composition B) at 110°–130° C. and then curing the mixtures at 135°–180° C. provided specimens for flexural testing in accordance with ASTM D-790, Method 1. The results were as follows:

| Composition | A | B |
|---|---|---|
| Modulus MSI | 0.58 | 0.57 |
| Strength KSI | 22.7 | 23.4 |
| Strain, % | 4.4 | 5.6 |

The foregoing properties typify advanced composite matrix resins.

The above-mentioned patents and publications (ASTM methods) are incorporated by reference. Obvious variations providing the same functional advantages are within the full intended scope of the appended claim.

What is claimed is:

1. The resinous polymer from N,N,N',N'-tetraglycidyl-1,3-propylene bis(p-aminobenzoate) and an aromatic polyamine.

2. The resinous polymer of claim 1, wherein said aromatic polyamine is selected from the group consisting of diaminodiphenyl sulfone and 1,3 propanediol bis-(p-aminobenzoate).